United States Patent
Lyon et al.

(10) Patent No.: US 6,812,834 B2
(45) Date of Patent: Nov. 2, 2004

(54) REFERENCE SAMPLE FOR GENERATING SMOKY ATMOSPHERE

(75) Inventors: Richard E. Lyon, Absecon, NJ (US); David R. Blake, Absecon, NJ (US)

(73) Assignee: The United States of America as represented by the Secretary of Transportation, Washington, DC (US)

( * ) Notice: Subject to any disclaimer, the term of this patent is extended or adjusted under 35 U.S.C. 154(b) by 107 days.

(21) Appl. No.: 10/046,734

(22) Filed: Jan. 17, 2002

(65) Prior Publication Data

US 2003/0131649 A1 Jul. 17, 2003

(51) Int. Cl.[7] .............................................. G08B 29/00
(52) U.S. Cl. ........................ 340/515; 73/1.03; 73/1.06; 436/9; 516/2
(58) Field of Search ............................... 73/1.03–1.07; 340/515; 436/9; 516/2–3

(56) References Cited

U.S. PATENT DOCUMENTS

| | | | | |
|---|---|---|---|---|
| 2,850,615 A | * | 9/1958 | Luse, Jr. et al. | 516/2 X |
| 3,250,723 A | * | 5/1966 | Fortney | 516/2 |
| 4,271,693 A | * | 6/1981 | Bute | 73/1.03 |
| 4,301,674 A | * | 11/1981 | Haines et al. | 73/1.05 |
| 4,866,425 A | * | 9/1989 | Lindmark | 340/556 |
| 4,980,571 A | * | 12/1990 | McRae et al. | 250/573 |
| 5,610,359 A | * | 3/1997 | Spector et al. | 516/2 X |
| 5,644,071 A | * | 7/1997 | Wagner | 73/1.06 X |
| 6,198,399 B1 | * | 3/2001 | Mattis | 340/515 X |
| 6,282,940 B1 | * | 9/2001 | Hung et al. | 73/1.06 |

FOREIGN PATENT DOCUMENTS

DE        2204801    *  8/1972   ........... G08B/21/00

* cited by examiner

*Primary Examiner*—Thomas P. Noland
(74) *Attorney, Agent, or Firm*—Otto M. Wildensteiner; James J. Drew

(57) ABSTRACT

A reference sample for testing fire detectors and a method of testing utilizing the reference samples. The reference sample comprises a fused mixture of pellets of the plastics usually found in aircraft cargo holds, with a heating element embedded in the sample. The pellets are in a plurality of layers with the composition of each layer being homogeneous but the thicknesses and porosities of the layers differing from each other. When the heating element is energized the layers of pellets, which have previously been fused into porous masses, begin to smolder, thereby generating a smoky atmosphere that as nearly as possible simulates the atmosphere in an aircraft cargo hold when there is a fire in the hold. In addition, a flammable liquid can be poured onto the sample and ignited, simultaneously with the energization of the heating element, by a separate ignition source to provide a flaming fire atmosphere.

4 Claims, 1 Drawing Sheet

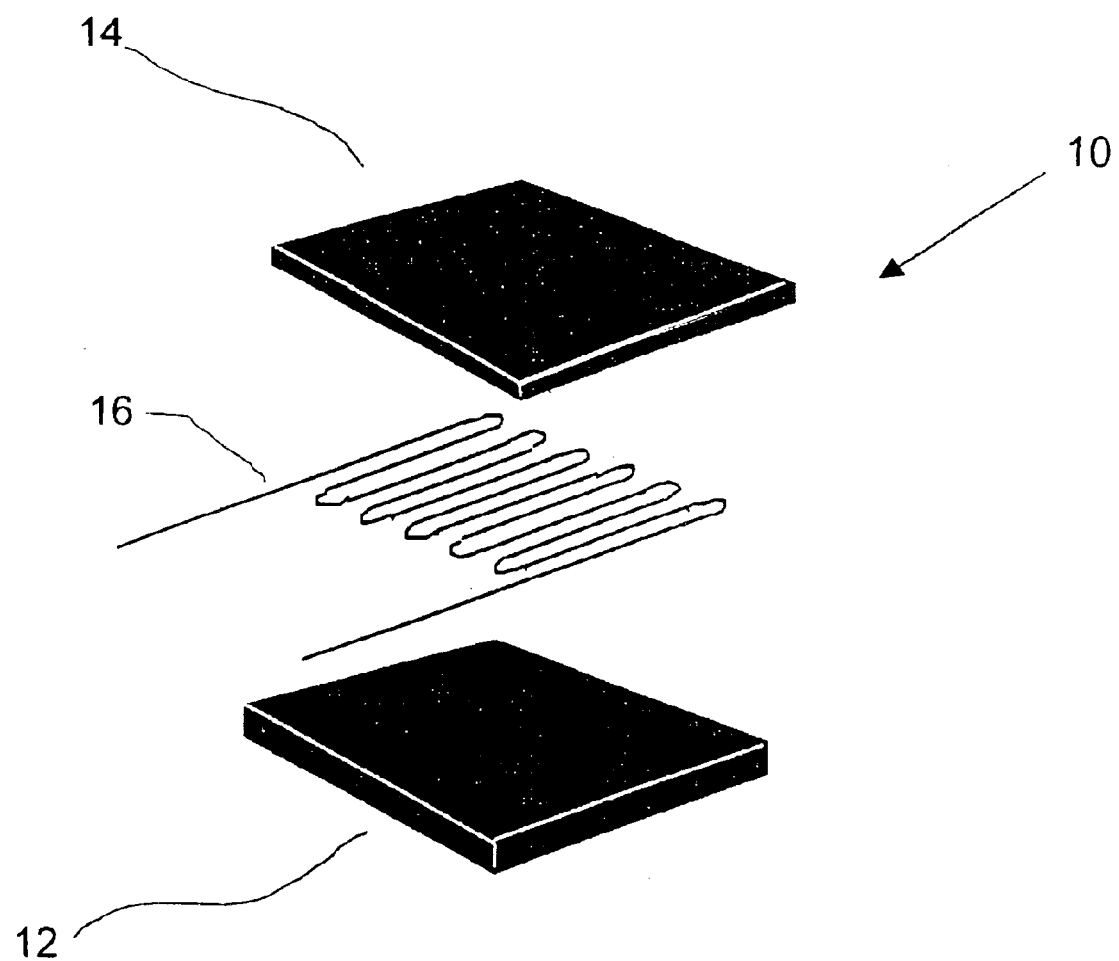

REFERENCE SAMPLE FOR GENERATING SMOKY ATMOSPHERE

STATEMENT OF GOVERNMENT INTEREST

The present invention may be made or used by or for the Government of the United States without the payment of any royalties thereon or therefor.

BACKGROUND

Fires in aircraft cargo holds are difficult to detect before they reach the stage where they endanger the safety of the aircraft. Sometimes they break out in the bottom of the hold, generating primarily smoke and other gases with little or no visible flames or heat for a considerable length of time. In addition, optical cargo hold detectors often generate "nuisance" alarms due to dust or moisture condensation inside the detector chamber. For this latter reason, it is felt that gas sensing detectors in combination with smoke detectors are preferable since this combination can discriminate between nuisance alarms and real fires.

A complication with gas sensing detectors is that due to the mix of materials in the hold, the composition of the gases generated by a fire can vary over wide ranges. Thus the detector manufacturers do not know what they must design their systems to respond to. There are prior art standards for smoke detectors but they are based on tests using shredded newspaper, wood, or flammable liquids as the burning substances. In passenger aircraft, however, the holds are filled primarily with luggage; thus the fires are initially fed by the synthetic plastics used in making the luggage and its contents.

Since luggage and its contents (clothing, consumer packaging, etc.) can be made from many different plastics, and each has its own characteristic products of combustion, allowing each detector manufacturer to use a different combustion test sample would lead to an undesirable variation in the types of detectors.

In addition, it is difficult to design a single detector that is effective with both smoldering and flaming fires, and it is likewise difficult to design a test setup that can simulate either type of fire.

OBJECTS OF THE INVENTION

Accordingly, it is an object of the present invention to provide a reference combustion test sample.

It is a further object of the present invention to provide a reference combustion test sample that generates, as closely as possible, the same mixture of products of combustion as would be found in a fire in an aircraft cargo hold.

It is a further object of the present invention to provide a reference combustion test sample that is easily prepared and easy to use.

It is a further object of the present invention to provide a reference combustion test sample that gives reproducible results.

It is a further object of the present invention to provide a reference combustion test sample that can be used to simulate both smoldering and flaming fires.

It is a further object of the present invention to provide a method of using a reference combustion test sample in a manner that simulates both smoldering and flaming fires.

SUMMARY

Briefly, the present invention is a reference combustion test sample that is comprised of pellets of different types of plastics that have been heated to fuse them into a porous unitary mass. A heating element is incorporated into the sample. When the heating element is energized it causes the sample to smolder, thereby simulating the atmosphere in a cargo hold when there is a smoldering fire in it. In addition, a flammable liquid can be placed on the sample and ignited simultaneously with the energization of the heating element to simulate a flaming fire.

BRIEF DESCRIPTION OF THE DRAWING

The only FIGURE is an exploded view of the reference sample of the present invention.

DESCRIPTION OF THE PREFERRED EMBODIMENT

The present invention is a composite reference material for combustion tests designed to aid in the design and testing of fire detectors, primarily for the cargo holds of airplanes. As can be imagined, the cargo holds of passenger airplanes are filled with luggage articles, including suitcases and their contents, which are made primarily from plastics. Therefore the reference combustion test sample is a composite made of beads of various synthetic plastics typically found in luggage.

It was determined through documentation of the construction and contents of unclaimed luggage that the plastic resins used in the construction of the reference combustion test sample were commonly found. The ratio of the individual plastic resin components were varied until the desired properties of the sample were achieved. Those properties included the generation of a steady plume of smoke very quickly after energization of the heating source and continued smoldering without transitioning into flaming combustion. The mix of plastic resins in the sample is as follows: 22.7 grams Polyvinylchloride (PVC) and 9.1 grams each Nylon 66, Polyethylene (PE), Polybutylene Terephthalate (PBT), Polystyrene (PS) and thermoplastic Polyurethane (PU). The sample also includes a heating element made of nichrome wire that is embedded in the sample.

To prepare sample 10, pellets of the above plastics 3–6 mm long and about 2 mm in diameter in the above proportions are thoroughly mixed and placed in two molds. The mold for bottom layer 12 is ¼ inch deep, the mold for top layer 14 is ⅛ inch deep; both molds are 4 inches square. The molds are filled with the proper quantities of pellets (17.2 grams for the ⅛ inch deep mold, 51 grams for the ¼ inch deep mold) and heated uncompressed at 180 degrees Celsius for 20 minutes. The pellets retain their shape at this temperature and simply stick together at their contact points. After this heating element 16, a length of 26 gauge nichrome wire formed into 15 passes back and forth 3 inches long and one quarter inch apart, is placed between the molds in contact with the fused pellets and the molds are simultaneously placed cavity to cavity and heated to 180 degrees C. and subjected to 5,000 pounds force for 20 minutes to form a "sandwich". The top and bottom molds contact each other along their perimeters; the resulting ⅜" high internal cavity maintains a constant volume after the mold perimeters contact each other and no further compression of the pellets occurs. The result is a sample of plastic of a certain composition and two different porosities with a heating element in it; the ends of the nichrome wire heating element project from the sample so that electrical leads can be attached. The porosity of the top layer is about 48% voids and the porosity of the bottom layer is about 22% voids (due to the relatively greater weight of pellets placed in the mold; i.e. the mold for bottom layer 12 is twice as deep as the mold for top layer 14 but it contains 3 times as many plastic beads).

The fact that the plastic sample is porous allows the smoke to almost immediately begin to emerge from it after it is heated by the nichrome heater. A solid sample would not begin to smoke until the surface was heated to the proper temperature, and thus would not produce the desired atmosphere as quickly.

When used for fire detector testing the sample is placed with the thin (and more porous) side up on a flat surface and the heater is energized, preferably with 42 volts AC. In 6 tests the samples generated smoke that reduced light transmittance by 15–29% within 38–46 seconds. This is important, since one of the detector criteria is the speed with which the detectors respond to a reduction in light transmittance to 96%. If the test samples were not uniform in their speed in generating the desired level of smoke, this would introduce an unacceptable variable in the testing and make meaningful comparisons difficult if not impossible.

If the samples are to be used in flaming combustion tests, a flammable liquid such as heptane can be poured on top of the sample and ignited with a spark generator. The additional mass of the lower part of the sample provides the mass necessary for longer-term testing.

We claim:

1. The method of generating a desired atmosphere for testing the response of a fire detector which comprises
    a) providing a porous sample;
    b) providing a heating element within said sample;
    c) energizing said heating element to cause said sample to release volatile thermal decomposition products to approximate smoldering;
    d) constructing said sample of a mixture of plastics; and,
    e) constructing said sample in a plurality of layers.

2. The method of claim 1 further comprising constructing said layers in different porosities.

3. The method of claim 2 further comprising construction said layers in different thicknesses.

4. The method of claim 3 further comprising placing said heating element in the interface between two of said layers.

* * * * *